United States Patent
Weaver et al.

(10) Patent No.: US 9,717,711 B2
(45) Date of Patent: Aug. 1, 2017

(54) **METHODS AND COMPOSITIONS FOR TREATING *CLOSTRIDIUM DIFFICILE* ASSOCIATED DISEASE**

(71) Applicant: The Lauridsen Group, Inc., Ankeny, IA (US)

(72) Inventors: Eric Weaver, Ankeny, IA (US); Abigail Henderson, Ankeny, IA (US); Christopher Detzel, Ankeny, IA (US)

(73) Assignee: The Lauridsen Group, Ankeny, IA (US)

( * ) Notice: Subject to any disclaimer, the term of this patent is extended or adjusted under 35 U.S.C. 154(b) by 0 days.

(21) Appl. No.: 14/741,173

(22) Filed: Jun. 16, 2015

(65) Prior Publication Data

US 2015/0359882 A1 Dec. 17, 2015

Related U.S. Application Data

(60) Provisional application No. 62/012,691, filed on Jun. 16, 2014.

(51) Int. Cl.

| | |
|---|---|
| *A61K 39/08* | (2006.01) |
| *A61K 31/4164* | (2006.01) |
| *A61K 45/06* | (2006.01) |
| *A61K 38/14* | (2006.01) |
| *C07K 16/00* | (2006.01) |
| *A23L 33/10* | (2016.01) |
| *A61K 39/00* | (2006.01) |

(52) U.S. Cl.
CPC .......... *A61K 31/4164* (2013.01); *A23L 33/10* (2016.08); *A61K 38/14* (2013.01); *A61K 45/06* (2013.01); *C07K 16/00* (2013.01); *A23V 2002/00* (2013.01); *A61K 2039/505* (2013.01)

(58) Field of Classification Search
None
See application file for complete search history.

(56) References Cited

U.S. PATENT DOCUMENTS

| | | |
|---|---|---|
| 5,773,000 A | 6/1998 | Bostwick et al. |
| 8,481,692 B2 | 7/2013 | Sidhu et al. |
| 2002/0009429 A1 | 1/2002 | Bostwick |
| 2009/0280134 A1 | 11/2009 | Holgersson et al. |
| 2010/0150942 A1 | 6/2010 | Cantor |
| 2011/0081347 A1 | 4/2011 | Gorlatov |
| 2011/0129479 A1 | 6/2011 | Tobin |
| 2012/0020950 A1 | 1/2012 | Davis et al. |
| 2013/0095057 A1 | 4/2013 | Johnson et al. |

FOREIGN PATENT DOCUMENTS

| | | |
|---|---|---|
| GB | 2482501 | 8/2012 |
| GB | 2482502 | 8/2012 |
| JP | 58216123 | 12/1983 |
| WO | 2012092469 | 7/2012 |
| WO | 2013028810 | 2/2013 |
| WO | 2013038156 | 3/2013 |

OTHER PUBLICATIONS

Kelly et al (Antimicrob. Agents and Chemo. 1996. 40(2): 373-9).*
Lyerly et al (Infec. Immun. 1991. 59(6): 2215-8).*
Salcedo et al (Gut. Sep. 1997 vol. 41, No. 3, pp. 366-370).*
Drew et al (2004. Poultry Science. 83: 414-420).*
Moore et al (Plos One. Jul. 2015. PLoS One 10(7): e0131829. doi:10.1371/journal.pone.0131829. pp. 1-16).*

* cited by examiner

*Primary Examiner* — Jennifer Graser
(74) *Attorney, Agent, or Firm* — Buchanan Ingersoll & Rooney PC

(57) ABSTRACT

The present invention provides methods for treating and preventing the reoccurrence of *C. diff* infection by administering an immunoglobulin concentrate in conjunction with a low protein diet.

15 Claims, 2 Drawing Sheets

METHODS AND COMPOSITIONS FOR TREATING *CLOSTRIDIUM DIFFICILE* ASSOCIATED DISEASE

BACKGROUND OF THE INVENTION

*Clostridium difficile*, also known as *C. difficile* or *C. diff*, is an anaerobic, gram positive, spore-forming *bacillus*. Under certain circumstances, *C. diff* colonizes the large bowel of patients and produces two cytotoxins, toxins A and B, that are responsible for causing diarrhea and colitis. The association between the release of these cytotoxins and antibiotic-associated diarrhea was first reported in 1978.

*Clostridium difficile*-associated disease, or CDAD, is caused by *C. difficile*. CDAD is sometimes referred to as *C. difficile* colitis or pseudomembranous colitis. CDAD is a disease that primarily threatens older patients in hospitals and elder care facilities. This virulent bacterial infection that causes severe diarrhea is quick to spread and difficult to remove from hospital and long term care environments. While those infected are often only mildly sick, CDAD can advance to a point where it irreversibly damages the colon. In severe cases, CDAD can cause sepsis, multiorgan failure, intestinal perforation, and even death. In fact, according to the Centers for Disease Control and Prevention (CDC), CDAD has caused more deaths in the United States than all other intestinal infections combined.

The incidence of CDAD has exploded in the last decade. As Clostridia are spore-forming bacteria, diarrheal patients in hospitals or other settings shed thousands of spores. These spores are resistant to most germicidal agents and can persist in hospital and nursing home wards for long periods of time. There is also concern that *C. diff* infection is becoming more prevalent outside of hospital settings (community-acquired), due to the emergence of hypervirulent and antibiotic resistant strains and that infection can and will occur in the absence of prior antibiotic exposure.

CDAD treatment often involves cessation of the inciting antibiotic, *C. difficile*-targeted antibiotic therapy, electrolyte normalization, fluid replacement, probiotics, and bile-acid sequestrants (e.g., cholestyramine). If CDAD continues despite stopping antibiotics, or if the diarrhea is severe, patients with CDAD are treated with antibiotics including metronidazole or oral vancomycin. Metronidazole is used as a first course of therapy and for more moderate cases of CDAD. Vancomycin, a more powerful therapy, is usually prescribed for more severe cases.

Knowledge of the epidemiology, pathogenesis and treatment of CDAD has increased substantially during the past three decades. However, this increased knowledge has not led to a decline in disease frequency or severity. To the contrary, since 2000, the incidence of CDAD and mortality rates from the disease have increased dramatically. These increases are fueled in part by microbial virulence and antibiotic resistance. However, host factors such as increasing age, disease co-morbidities and immune senescence as well as environmental factors such as antibiotic use and contamination of healthcare facilities by *C. difficile* spores are also instrumental. These developments (increasing CDAD incidence, severity and death rates) clearly demonstrate that current approaches to disease prevention and treatment are inadequate and that new approaches are needed.

It is therefore a primary objective of the present invention to provide an improved method and means of treating CDAD.

It is a further objective of the present invention to provide a method of preventing reoccurrence of *C. diff* infection following its initial successful treatment.

These and other objects of the invention will become apparent from the detailed description of the invention which follows.

SUMMARY OF THE INVENTION

According to the invention, the applicant has provided a unique method of treating *Clostridium difficile* associated disease (CDAD) which involves, 1) treatment with a low protein diet and; 2) administering immunoglobulin concentrate (IgC). The protein intake is limited to ≤75% of the protein requirement with 20-50% of the restricted protein intake comprising immunoglobulin concentrate. Under fatal CDAD conditions treatment in the manner described herein significantly improved symptoms and rate of survival. The invention is further directed to methods of preventing the reoccurrence of CDAD by administering IgC and a low protein diet for several weeks following successful initial treatment of the infection.

DETAILED DESCRIPTION OF THE DRAWINGS

Figure 3:
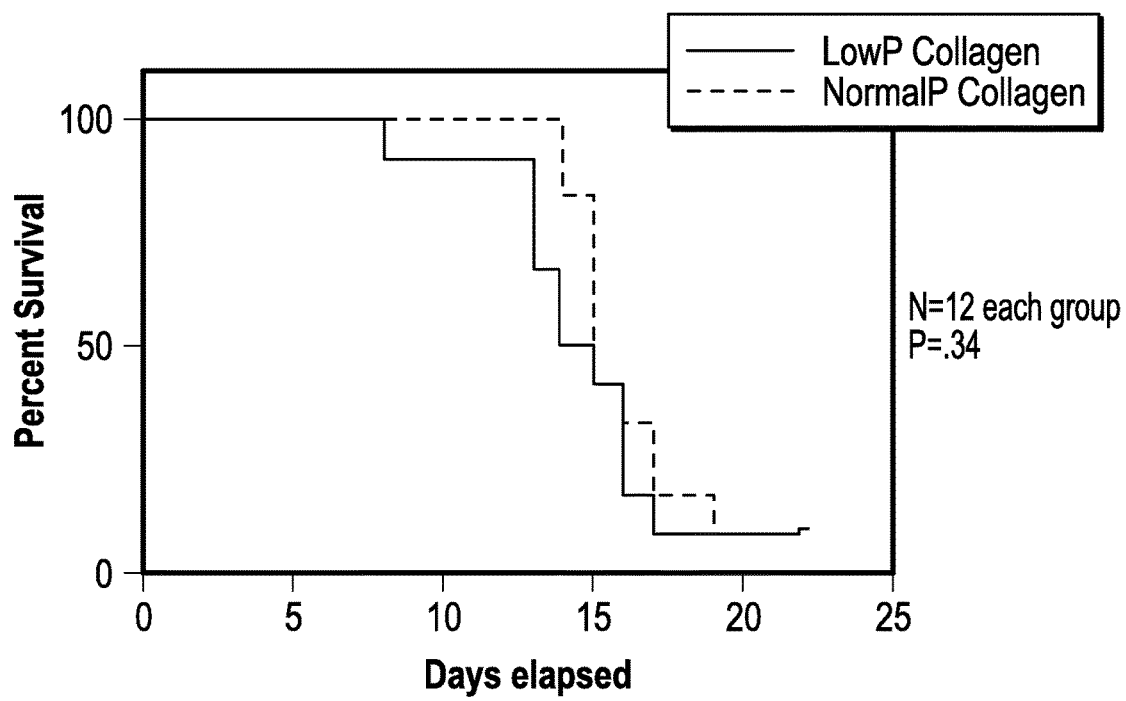

FIG. 3 is a graph showing the percent survival of mice consuming low protein diets providing 25% of the daily protein requirement and supplemented with 2 g of hydrolyzed collagen (HC)/Kg body weight/day in comparison to diets meeting protein requirements and supplemented with 2 g of HC/Kg body weight/day in accordance with the Example.

Figure 4:
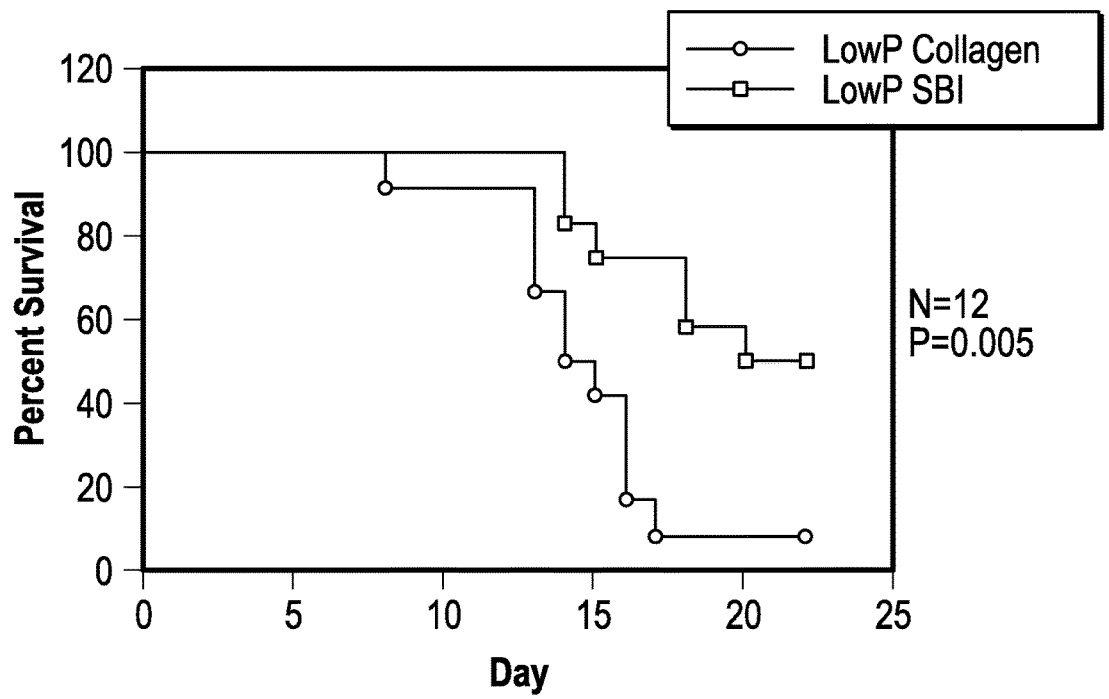

FIG. 4 is a graph showing the percent survival of mice consuming a low protein diet (25% of the daily protein requirement) supplemented with hydrolyzed collagen (HC) in comparison to a low protein diet supplemented with IgC in accordance with the Example.

DETAILED DESCRIPTION OF THE INVENTION

The present invention relates to a method of treating CDAD and preventing CDAD reoccurrence with a combination of immunoglobulin concentrate (IgC) and a low protein diet. The inventors have surprisingly discovered that animals treated with IgC to provide 20-50% of the daily protein intake whereby the total daily protein intake is limited to ≤75% of the protein requirement have significantly higher rates of survival versus those treated only with IgC, or those treated only with a low protein diet. The normal protein requirement (30 g of Protein/Kg body weight/day) was estimated using standards described in Nutrient Requirements of Laboratory Animals and average mouse body weights (19.5 g) measured at the beginning of the study. The relevant text of Nutrient Requirements of Laboratory Animals. Washington D.C., USA: National Academies Press, 1995. ProQuest ebrary. Web. 15 Jun. 2015, is hereby specifically incorporated by reference.

According to the invention, Applicant has provided herein a pharmaceutical composition comprising immunoglobulin components purified and concentrated from animal plasma which are useful in reducing *C. difficile*-induced mortality. While serum-derived bovine immunoglobulin protein isolate (SBI) is a preferred IgC for use in the invention, the invention contemplates the use of immunoglobulin concentrate from any source. The IgC generally contains 60% or more by weight immunoglobulins with the balance being other serum proteins, such as albumin, transferrin, etc.

According to the invention, gamma-globulin isolated from animal sources such as serum, plasma, egg, or milk is administered orally for treatment of *C. diff* infection or CDAD. As used herein with reference to the composition of the invention, the terms "plasma", "globulin", "gamma-globulin", and "immunoglobulin" will all be used. These are all intended to describe a composition purified from animal sources including blood, egg, or milk-which retains the Fc region of the immunoglobulin molecule. This also includes transgenic recombinant immunoglobulins purified from transgenic bacteria, plants or animals. This can be administered by spray-dried plasma, or globulin which has been further purified therefrom, or any other source of serum globulin which is available. The immunoglobulin of this invention is provided in the form of IgC, with serum bovine immunoglobulin (SBI) being a preferred source thereof.

Globulin may be purified according to any of a number of methods available in the art, including those described in Akita, B. M. and S, Nakai. 1993. Comparison of four purification methods for the production of immunoglobulins from eggs laid by hens immunized with an enterotoxigenic *E. coli* strain. Journal of Immunological Methods 160:207-214; Steinbuch, M. and R. Audran. 1969. The isolation of IgG from mammalian sera with the aid of caprylic acid. Archives of Biochemistry and Biophysics 134:279-284; Lee, Y., T. Aishima, S, Nakai, and J. S. Sim. 1987. Optimization for selective fractionation of bovine blood plasma proteins using polyethylene glycol. Journal of Agricultural and Food Chemistry 35:958-962; Poison, A., G. M. Potgieter, J. F. Langier, G. E. F. Mears, and F. J. Toubert. 1964. Biochem. Biophys. Acta. 82:463-475.

Animal plasma from which immunoglobulin or other plasma fractions may be isolated include porcine, bovine, ovine, poultry, equine, or goat plasma. Additionally, applicants have identified that cross species sources of the gamma globulins still provides the effects of the invention.

Concentrates of the product can be obtained by spray drying, lyophilization, or any other drying method that does not cause the plasma to lose its ability to treat infection caused by *C. diff* The concentrates may also be used in their liquid or frozen form.

The active ingredient may also be microencapsulated, protecting and stabilizing from high temperature, oxidants, enteric digestion, etc. The pharmaceutical compositions of the invention can be in tablets, capsules, ampules for oral use, granulate powder, cream, both as a unique ingredient and associated with other excipients or active compounds, or even as a feed additive.

One method of achieving a gamma-globulin composition concentrate of the invention is as follows although the globulin may be delivered as a component of plasma.

The immunoglobulin concentrate is derived from animal blood. The source of the blood can be from any animal that has blood which includes plasma and immunoglobulins. For convenience, blood from beef, pork, and poultry processing plants is preferred. Anticoagulant is added to whole blood and then the blood is centrifuged to separate the plasma. Any anticoagulant may be used for this purpose, including sodium citrate and heparin. Persons skilled in the art can readily appreciate such anticoagulants. Calcium or other suitable reagent to react with fibrinogen is then added to the plasma to promote precipitation, or to facilitate the removal of fibrinogen; however other methods are acceptable. This mixture is then centrifuged to remove the fibrin portion.

Once the fibrin is removed from plasma resulting in serum, the serum can be used as a principal source of Ig. The fibrinogen depleted plasma is next treated with an amount of salt compound or polymer sufficient to precipitate the albumin or globulin fraction of the plasma. Examples of phosphate compounds which may be used for this purpose include all polyphosphates, including sodium hexametaphosphate and potassium polyphosphate. The globulin may also be isolated through the addition of polyethylene glycol or ammonium sulfate.

Following the addition of the phosphate compound, the pH of the plasma solution is lowered to stabilize the albumin precipitate. Any type of acid can be used for this purpose, so long as it is compatible with the plasma solution. Persons skilled in the art can readily ascertain such acids. Examples of suitable acids include, but are not limited to, HCl, acetic acid, $H_2SO_4$, citric acid, and $H_2PO_4$. The acid is added in an amount sufficient to lower the pH of the plasma to the designated range. Generally, this amount will range from a ratio of about 1:4 to 1:2 acid to plasma. The plasma is then centrifuged to separate the globulin fraction from the albumin fraction.

The next step in the process is to raise the pH of the globulin fraction with a base until it is no longer corrosive to separation equipment. Acceptable bases for this purpose include NaOH, KOH, and other alkaline bases. Such bases are readily ascertainable by those skilled in the art. The pH of the globulin fraction is raised until it is within a non-corrosive range which will generally be between 5.0 and 9.0.

The final immunoglobulin concentrate can optionally be spray-dried or lyophilized into a powder. The powder allows for easier packaging and the product remains stable for a longer period of time than the raw globulin concentrate in liquid or frozen form. The immunoglobulin concentrate powder has been found to contain approximately 40-55% by weight IgG, 1-2% by weight IgA, and 6-8% by weight IgM. At a minimum, the immunoglobulin concentrate of the invention should contain at least 40% by weight IgG, with at least 50% by weight IgG being preferred, and at least 55% by weight being most preferred.

In addition to administration with conventional carriers, active ingredients may be administered by a variety of specialized delivery drug techniques which are known to those of skill in the art.

Those skilled in the medical arts will readily appreciate that the doses and schedules of the immunoglobulin and protein intake will vary depending on the age, health, sex, size and weight of the patient rather than administration, etc. These parameters can be determined for each system by well-established procedures and analysis e.g., in phase I, II, and III clinical trials.

In accordance with certain embodiments of the invention, the immunoglobulin concentrate may be administered through oral consumption in an amount sufficient to reduce, attenuate, or inhibit the effects of *C. diff* infection. In this regard, Ig concentrate (IgC) should be administered in an amount sufficient to reduce adverse symptoms of *C. diff* infection. In one embodiment, the IgC is administered to provide about 0.10-3.0 g of protein/kg/day, taking into account animal species, daily protein requirement, and protein obtained from other sources. In the preferred embodiment, the IgC is administered to humans to provide about 0.001-0.24 g of protein/kg/day. Dose conversions between animal species can be estimated using FDA guidance for Dose conversion in clinical trails, the relevant text of which is specifically incorporated by reference. Guidance for Industry Estimating the Maximum Safe Starting Dose in Initial Clinical Trials for Therapeutics in Adult Healthy Volunteers, Pharmacology and Toxicology, U.S. Department of Health and Human Services Food and Drug Administration Center for Drug Evaluation and Research (CDER), July 2005. As used herein, the term "C. diff infection" means overgrowth of Clostridium difficile bacterium sufficient to cause adverse symptoms such as, but not limited to, diarrhea, abdominal pain, weight loss, colitis, fever, elevated white blood cells, vomiting, and/or dehydration.

The invention may also be used prophylactically to prevent C. diff infection. In this regard, the IgC/low protein diet may be administered in the same doses described above up to several weeks prior to a potential C. diff infection. In one embodiment, the invention is provided two or more weeks prior to a potential C. diff infection.

The invention may also be used to prevent the reoccurance of C. diff immediately following successful treatment of an initial C. diff infection. In this regard, the IgC/low protein diet may be administered in the same doses described above up to several weeks following treatment of an initial C. diff infection. In one embodiment, the invention is provided two or more weeks following successful treatment of an initial C. diff infection.

While the IgC of the invention is preferably administered orally or by tube feeding, other modes of invention are contemplated for use in the invention as well, such as delivery by suppository or enema. The doses may be provided once daily, or divided and administered twelve hours apart, for example. More frequent dosing regimes may be necessary for optimum effectiveness.

The globulin concentrate can be combined with a pharmaceutically acceptable carrier such as a suitable liquid vehicle or excipient and an optional auxiliary additive or additives. The liquid vehicles and excipients are conventional and are commercially available. Illustrative thereof are distilled water, physiological saline, aqueous solutions of dextrose and the like.

The immunoglobulin composition of this invention may be administered alone or in conjunction with other therapeutic agents used in the treatment of microbial infections and associated symptoms, either in a kit for combination therapy or combined in the same pharmaceutical dosage form. Such additional therapeutic agents would include, but are not limited to, antibiotics, analgesics, antivirals, NSAIDS, corticosteroids, etc. Any type of medication may be used in this regard so long as it is compatible with the plasma fraction and does not substantially limit or decrease its efficacy in the reduction of symptoms of C. diff infection.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Dragee cores may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet of dragee coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids; such as fatty oils, liquid paraffin, or liquid polyethylene glycols. In addition stabilizers may be added.

The therapeutic administration of oral doses of globulin concentrate in combination with low protein intake according to the invention were found to decrease symptoms of C. diff infection and reduce C. diff-induced mortality. As used herein, "low protein diet" is defined as a diet whereby the person receives ≤75% of its daily protein requirement, or less than about 15 g of protein/100 g diet. In another embodiment, the person receives ≤50% of its daily protein requirement, or less than about 10 g of protein/100 g diet. In another embodiment, the person receives ≤25% of its daily protein requirement, or less than about 5 g of protein/100 g diet. The inventors surprisingly determined that animals that received either a low protein diet or IgC did not achieve the synergistic effect of reduction of mortality achieved by animals that received both a low protein diet and IgC in the treatment of CDAD.

The person can be treated with the IgC/low protein diet for a time period sufficient to treat the C. diff infection and/or improve the symptoms of the infection. In one embodiment, the person is treated for a time period of at least 7 days. In a preferred embodiment, the person is treated for a time period of at least 10 days. There is no maximum length of time the person may be treated with the IgC/low protein diet combination except to the extent the harm that may come from ingestion of a low protein diet for an extended period of time outweighs the potential harm from the C. diff infection.

The following example is intended to illustrate certain embodiments of the invention without limitation.

EXAMPLE

Effects of Bovine Immunoglobulin Concentrate on Recurrent Clostridium difficile Associated Disease (CDAD) in Mice A mouse model to mimic human CDAD was developed by Chen et al. Chen X, Katchar K, Goldsmith J D, Nanthalcumar N, Cheknis A, Gerding D N, Kelly C P. A mouse model of Clostridium difficile-associated disease. Gastroenterology 2008; 135(6): 1984-92. Briefly mice were administered a cocktail of antibiotics (kanamycin, gentamicin, colistin, metronidazole, and vancomycin followed by clindamycin phosphate two days later) to disrupt the normal flora. Next mice were challenged with C. difficile (VPI10463) at one time and administered vancomycin for five days. Vancomycin is the standard of care for eradicating C. difficile in human patients. Kaplan-Meier survival curves indicated that the $10^5$ colony forming unit (CFU) dose of C. difficile induced 96% mortality by day 4. Evidence of similarities to human CDAD were shown histologically.

Mouse tissues displayed features of pseudomembranous colitis including submucosa edema, epithelial necrosis, mucosal proliferation and inflammatory infiltrate. This mouse model closely resembles CDAD observed in humans, in that it is induced by antibiotics, severity of disease depends on challenge and histological features are similar to pseudomembranous colitis.

Study Description:
Evaluation of IgC in Protecting Mice Against Recurrent CDAD
Experimental Design and Method:

C57BL/6 mice (average body weight equal to 19.5) were housed in cages with free access to chow (Purina 5000) and tap water. Animals were assigned to regular chow (a diet providing the recommended daily protein amount, e.g. 30 g of Protein/Kg body weight/day) or to a low protein diet that provided 25% of the recommended daily protein intake on Day −13. Treatment with 2 g of Protein/Kg body weight/day of bovine IgC (SBI) or protein control (hydrolyzed collagen (HC)) began on Day −13. Animals were treated with a mixture of oral antibiotics (kanamycin, gentamicin, colistin, metronidazole, and vancomycin) for 3 days (beginning on Day −5) as previously described. Chen X, Katchar K, Goldsmith J D, Nanthalcumar N, Cheknis A, Gerding D N, Kelly C P. A mouse model of Clostridium difficile-associated disease. Gastroenterology 2008; 135(6): 1984-92. Two days later, they were given parenteral clindamycin phosphate (10 mg/kg s.c.) [Day −1]. One day later [Day 0] they were challenged by gavage with ~$10^5$ cfu of toxogenic C difficile [strain 10465]. From Day 0 to Day 4 all animals were treated with vancomycin 10 mg/kg (added to gavage fluid). A moderate to severe colitis resulted and developed 1 to 5 days after the administration of C. difficile. Untreated, the majority of animals develop severe colitis which may be fatal.

Figure 1:
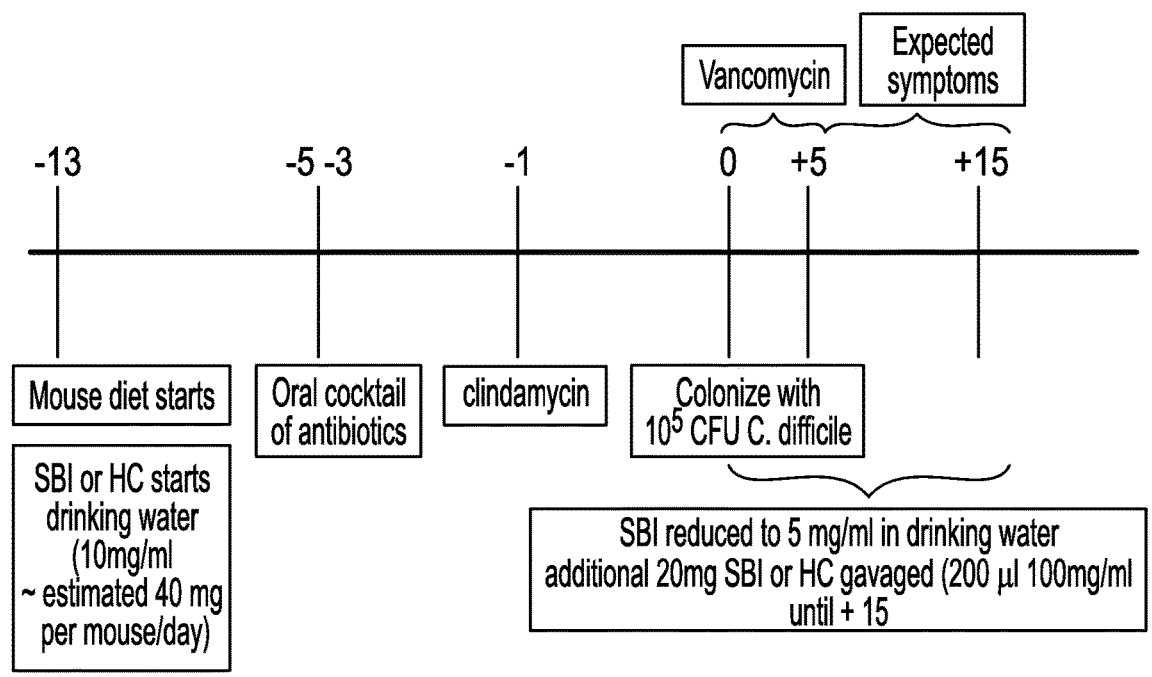
FIG. 1 is a schematic of a timeline to study antibiotic induced CDAD in mice in accordance with the Example.

The test compound consisted of IgC, or HC, mixed in drinking water during the entire course of the experiment (Days −13 to +15) and supplemented by daily oral gavage during days 0 to +15. To achieve a daily intake of 40 mg (i.e. 2 g of Protein/Kg of body weight/day for a 20 g mouse) IgC, of HC, was mixed in drinking water at a concentration of 10 mg/mL (assuming a daily fluid intake of 3 to 5 mL) during days −13 to −1. Beginning on Day 0 through the end of the study IgC, or HC, was administered both through mixture in drinking water and oral gavage. From Day 0 to +15 SBI, or HC, was mixed in drinking water at a concentration of 5 mg/mL (providing 20 mg perday assuming a daily fluid intake of 3 to 5 mL), with an additional 20 mg of IgC, or HC, provided to animals by oral gavage (200 μL of IgC or HC at a concentration of 100 mg/mL). The IgC, or HC, drinking mixtures (25 mL per animal per day) were changed daily. A schematic of the study timeline is shown in FIG. 1.

TABLE 1

Experimental groups and dosing schedule

| Group No. | n= | Diet (% protein) | Treatments | ABX & [a, b, c, d] C. difficile | Route of administration | Days of dosing [c] |
|---|---|---|---|---|---|---|
| 1 | 12 | 5% | Collagen 40 mg/day | Yes | po/gavage | −13 to +15 |
| 2 | 12 | 5% | IgC 40 mg/day | Yes | po/gavage | −13 to +15 |
| 3 | 12 | 20% | Collagen 40 mg/day | Yes | po/gavage | −13 to +15 |
| 4 | 12 | 20% | IgC 40 mg/day | Yes | po/gavage | −13 to +15 |

[a] On Days −5, −4 and −3 the ABX & C. difficile animals received an antibiotic cocktail
[b] On Day −1 the ABX & C. difficile animals received clindamycin (10 mg/kg s.c.)
[c] On Day 0 all animals received gavage with ~$10^5$ cfu of C difficile
[d] All animals were treated with vancomycin 10 mg/kg (added to gavage fluid). Vancomycin dosing (mixed with gavage fluid) commenced on the day of C. difficile challenge (Day 0) and continued daily for 5 days (to Day 4).

The animals were weighed daily and observed three times daily for morbidity and presence or absence of diarrhea. Animals judged to be in a moribund state [extended period of weight loss progressing to an emaciated state, anorexia for 24-48 hrs, prolonged lethargy (more than 3 days), signs of paralysis, skin erosions or trauma, hunched posture, distended abdomen] were euthanized by a single injection of sodium pentobarbital.

Outcomes:
Standard outcome
Animal survival
Results

Figure 2:
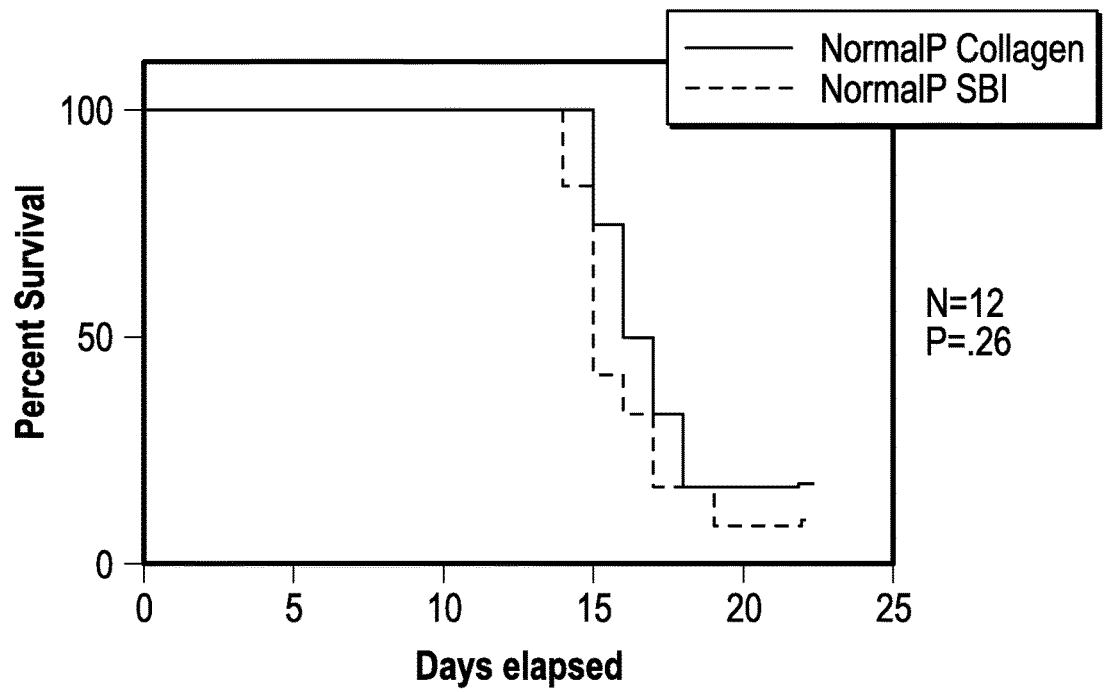
FIG. 2 is a graph showing the percent survival of mice consuming diets meeting protein requirements (e.g. 30 g of Protein/Kg body weight/day) supplemented with 2 g of hydrolyzed collagen (HC)/Kg body weight/day or 2 g of IgC/Kg body weight/day in accordance with the Example.

Mice receiving the recommended daily protein requirement (e.g. 30 g of Protein/Kg body weight/day) did not have differences in survival rates between the IgC and HC groups (FIG. 2), indicating that IgC alone does not provide adequate protection against CDAD. In addition, mice that received the low protein diet (25% of the recommended daily protein requirement) and HC had an earlier onset of CDAD compared with mice receiving the normal diet and HC. However, there was no difference in mortality indicating protection was not due to low protein alone, FIG. 3. Results indicate that malnourished mice with C. difficile that are treated with a low protein diet and IgC are unexpectedly protected from CDAD-induced mortality (FIG. 4).

Without all of the necessary data to support the hypothesis of the mechanism, the unexpected finding that lowering dietary protein to less than 75% of the protein requirement when combined with IgC supported higher survival rates is important to the management of hospitalized patients or those treated with antibiotics. Protein restriction may be increasing amino acid digestibility and thus reducing protein and nitrogen concentrations in the colon. IgC may be further altering nutrient supply or luminal conditions which favors a microbiome limiting the colonization of *C. difficile*.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of preventing the reoccurrence of *Clostridium difficile* (*C. diff*) infection in a subject that has previously been treated for an initial *C. diff* infection, the method comprising: administering to the subject an immunoglobulin concentrate (IgC) and a low protein diet for a time period sufficient to prevent reoccurrence of the *C. diff* infection, wherein the IgC comprises gamma-globulin isolated from an animal source selected from serum, plasma, egg, or milk; wherein the IgC comprises at least 40% IgG by weight; and wherein the low protein diet provides ≤75% of the subject's daily protein requirement.

2. The method of claim 1 whereby the IgC and low protein diet are administered for a time period of at least two weeks.

3. The method of claim 1 whereby the IgC is administered in an amount sufficient to provide a total of about 0.10-3.0 g of protein/kg/day.

4. The method of claim 1 whereby the IgC is administered in an amount sufficient to provide a total of about 0.001-0.24 g of protein/kg/day.

5. The method of claim 1 whereby the low protein diet provides ≤50% of the subject's daily protein requirement.

6. The method of claim 1 whereby the low protein diet provides ≤25% of the subject'daily protein requirement.

7. The method of claim 1 whereby the IgC comprises at least 60% by weight immunoglobulins.

8. The method of claim 1 whereby the immunoglobulin concentrate is serum bovine immunoglobulin.

9. The method of claim 1 whereby the *C. diff* infection in the subject was previously treated with at least one antibiotic.

10. The method of claim 9 whereby the *C. diff* infection in the subject was previously treated with one or more antibiotics selected from the group consisting of vancomycin and metronidazole.

11. The method of claim 1 whereby the *C. diff* infection in the subject was previously treated by administering a low protein diet and an immunoglobulin concentrate (IgC) in an amount sufficient to reduce, attenuate, or inhibit the effects of *C. diff* infection.

12. The method of claim 1 whereby the IgC is administered orally.

13. The method of claim 1 whereby the IgC provides at least 20% of the subject's total protein.

14. The method of claim 1 whereby the IgC and low protein diet are administered for a time period of at least 7 days.

15. The method of claim 1 whereby the IgC and low protein diet are administered for a time period of at least 10 days.

* * * * *